US008809233B2

(12) United States Patent
Griveau et al.

(10) Patent No.: US 8,809,233 B2
(45) Date of Patent: *Aug. 19, 2014

(54) TERNARY HERBICIDAL COMPOSITIONS COMPRISING AMINOPYRALID AND IMAZAMOX

(75) Inventors: Yannick Griveau, Alsemberg (BE); Hagen Bremer, Roemerberg (DE); Matthias Pfenning, Schwegenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/999,328

(22) PCT Filed: Jun. 16, 2009

(86) PCT No.: PCT/EP2009/057408
§ 371 (c)(1),
(2), (4) Date: Dec. 16, 2010

(87) PCT Pub. No.: WO2009/153246
PCT Pub. Date: Dec. 23, 2009

(65) Prior Publication Data
US 2011/0092366 A1  Apr. 21, 2011

(30) Foreign Application Priority Data
Jun. 18, 2008  (EP) .................................. 08158502

(51) Int. Cl.
*A01N 43/40* (2006.01)
(52) U.S. Cl.
USPC ........................................................ 504/130
(58) Field of Classification Search
None
See application file for complete search history.

(56) References Cited

U.S. PATENT DOCUMENTS

| 5,973,154 A | 10/1999 | Drabb et al. |
| 6,339,158 B1 | 1/2002 | Wepplo et al. |
| 2002/0002113 A1 | 1/2002 | Jones |
| 2004/0033897 A1* | 2/2004 | Haas .............................. 504/255 |
| 2010/0041553 A1 | 2/2010 | Palma et al. |

FOREIGN PATENT DOCUMENTS

| AU | 612347 | 8/1988 |
| EP | 290354 | 11/1988 |
| WO | WO 96/32013 | 10/1996 |
| WO | WO 01/51468 | 7/2001 |
| WO | WO 2005/096814 | 10/2005 |
| WO | WO 2007/071655 | 6/2007 |
| WO | WO 2007/071730 | 6/2007 |
| WO | WO-2007071655 | * 6/2007 |
| WO | WO 2007/112505 | 10/2007 |
| WO | WO 2008/058622 | 5/2008 |
| WO | WO 2008/121200 | 10/2008 |
| WO | WO 2009/153247 | 12/2009 |

OTHER PUBLICATIONS

Kelley Kevin et al. "Soybean response to plant growth regulator herbicides is affected by other postemergence herbicides", Weed Science, 53:1, (2005), 101-112, XP002605493.
Bukun et al., "Aminopyralid and Clopyralid Absorption and Translocation in Canada Thistle (Cirsium Arvense)," Weed Science, vol. 57, (Jan. 1, 2009), pp. 10-15.

* cited by examiner

*Primary Examiner* — Alton Pryor
(74) *Attorney, Agent, or Firm* — Brinks Gilson & Lione

(57) ABSTRACT

Herbicidally active compositions, which comprise 4-amino-3,6-dichloropyridine-2-carboxylic acid (common name: aminopyralid), 2-[(RS)-4-isopropyl-4-methyl-5-oxo-2-imidazolin-2-yl]-5-methoxymethylnicotinic acid (common name: imazamox)
and
at least one herbicide B from the group of the lipid biosynthesis inhibitors, acetohydroxyacid synthase inhibitors, carotenoid biosynthesis inhibitors, auxin herbicides, mitosis inhibitors, protoporphyrinogen IX oxidase inhibitors, growth substances, and a variety of other herbicides selected from aziprotryn, barban, bensulide, benzthiazuron, benzofluor, buminafos, buthidazole, buturon, cafenstrole, chlorbufam, xhlorofenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triazofenamide, triaziflam or trimeturon,
a method for controlling undesirable vegetation, their use for controlling undesirable vegetation, and formulations comprising such compositions.

20 Claims, No Drawings

TERNARY HERBICIDAL COMPOSITIONS COMPRISING AMINOPYRALID AND IMAZAMOX

This application is a National Stage application of International Application No. PCT/EP2009/057408 filed Jun. 16, 2009, the entire contents of which is hereby incorporated herein by reference. This application also claims priority under 35 U.S.C. §119 to European Patent Application No. 08158502.8, filed Jun. 18, 2008, the entire contents of which is hereby incorporated herein by reference.

The present invention relates to herbicidally active compositions, which comprise 4-amino-3,6-dichloropyridine-2-carboxylic acid (common name: aminopyralid), 2-[(RS)-4-isopropyl-4-methyl-5-oxo-2-imidazolin-2-yl]-5-methoxymethylnicotinic acid (common name: imazamox) and at least one herbicide B.

In crop protection, it is desirable in principle to increase the specificity and the reliability of the action of active compounds. In particular, it is desirable for the crop protection product to control the harmful plants effectively and, at the same time, to be tolerated by the useful plants in question.

Amino-3,6-dichloropyridine-2-carboxylic acid (common name: aminopyralid; formula I), its manufacture and its herbicidal action was described in WO 01/51468.

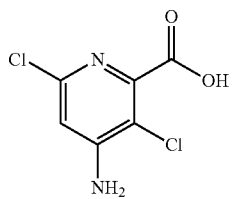

2-[(RS)-4-isopropyl-4-methyl-5-oxo-2-imidazolin-2-yl]-5-methoxymethylnicotinic acid (common name: imazamox; formula II) is an active compound from the group of imidazolinone herbicides, which are known e.g. from Shaner, D. L. O'Conner, S. L The Imidazolinone Herbicides, CRC Press Inc., Boca Raton, Fla. 1991 and also from The Compendium of Pesticide Common Names http://www.alanwood.net/pesticides/.

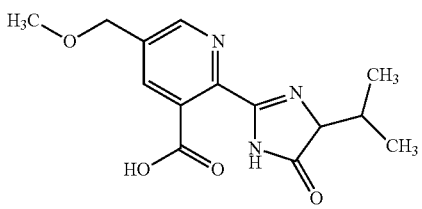

The combination of aminopyralid and imazamox is described in WO 2007/071655.

Although aminopyralid is a highly effective post-emergence herbicide, in many cases it does not provide a sufficient control of the relevant harmful plants and its activity at low application rates is not always satisfactory. Moreover, aminopyralid is known to have a post-emergence activity. Apart from that, its compatibility with certain dicotyledonous crop plants such as cotton, sunflower, soybean, *brassica* crops such as canola and oilseed rape and some graminaceous plants such as rice, wheat, rye and barley is not always satisfactory, i.e. in addition to the harmful plants, the crop plants are also damaged to an extent which is not acceptable. Though it is in principle possible to spare crop plants by lowering the application rates, the extent of the control of harmful plants is naturally also reduced.

It is known that combined application of certain different herbicides with specific action might result in an enhanced activity of an herbicide component in comparison with a simple additive action. Such an enhanced activity is also termed a synergism or synergistic activity. As a consequence, it is possible to reduce the application rates of herbicidally active compounds required for controlling the harmful plants.

It is an object of the present invention to provide herbicidal compositions, which show enhanced herbicide action in comparison with the herbicide action of imazamox and aminopyralid against undesirable harmful plants, in particular against *Alopecurus myosuroides, Apera spica-venti, Papaver rohes, Geranium* spec, *Brassica* spec, *Avena fatua, Bromus* spec., *Echinocloa* spec. *Lolium* spec., *Phalaris* spec., *Setaria* spec., *Digitaria* spec., *brachiaria* spec., *Amaranthus* spec., *Chenopodium* spec., *Abutilon theophrasti, Galium aparine, Veronica* spec., or *Solanum* spec. and/or to improve their compatibility with crop plants, in particular improved compatibility with wheat, barley, corn (maize), rye, rice, soybean, sunflower, *brassica* crops and/or cotton. The composition should also have a good pre-emergence herbicidal activity.

We have found that this object is achieved, by herbicidally active compositions comprising a) the combination of aminopyralid, i.e. 4-amino-3,6-dichloropyridine-2-carboxylic acid and imazamox, i.e. 2-[(RS)-4-isopropyl-4-methyl-5-oxo-2-imidazolin-2-yl]-5-methoxymethylnicotinic acid (collectively hereinafter also referred to as herbicide A);

and b) at least one herbicide B from the group of the lipid biosynthesis inhibitors, acetohydroxyacid synthase inhibitors, carotenoid biosynthesis inhibitors, auxin herbicides, mitosis inhibitors, protoporphyrinogen IX oxidase inhibitors, growth substances, and a variety of other herbicides selected from aziprotryn, barban, bensulide, benzthiazuron, benzofluor, buminafos, buthidazole, buturon, cafenstrole, chlorbufam, chlorofenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triazofenamide, triaziflam or trimeturon.

The invention relates in particular to compositions in the form of herbicidally active compositions as defined above.

The invention furthermore relates to the use of compositions as defined herein for controlling undesirable vegetation in crops. When using the compositions of the invention for this purpose the herbicide A and the at least one herbicide B can be applied simultaneously or in succession in crops, where undesirable vegetation may occur.

The invention furthermore relates to the use of compositions as defined herein for controlling undesirable vegetation in crops which, by genetic engineering or by breeding, are resistant to one or more herbicides, e.g. glyphosate and glyfosinate, and/or to pathogens such as plant-pathogenous fungi, and/or to attack by insects; preferably resistant to one or more herbicides that act as acetohydroxyacid synthase inhibitors.

The invention furthermore relates to a method for controlling undesirable vegetation, which comprises applying an herbicidal composition according to the present invention to the undesirable plants. Application can be done before, during and/or after, preferably during and/or after, the emergence of the undesirable plants. The herbicide A and the at least one herbicide B can be applied simultaneously or in succession.

The invention in particular relates to a method for controlling undesirable vegetation in crops, which comprises applying an herbicidal composition according to the present invention in crops where undesirable vegetation occurs or might occur.

The invention furthermore relates to a method for controlling undesirable vegetation, which comprises allowing a composition according to the present invention to act on plants, their habitat or on seed.

In the methods of the present invention it is immaterial whether the herbicide A and the at least one herbicide B are formulated and applied jointly or separately, and, in the case of separate application, in which order the application takes place. It is only necessary, that the herbicide A and the at least one herbicide B are applied in a time frame, which allows simultaneous action of the active ingredients on the plants.

The invention also relates to an herbicide formulation, which comprises a herbicidally active composition as defined herein and at least one carrier material, including liquid and/or solid carrier materials.

The compositions according to the invention have better herbicidal activity against harmful plants than would have been expected by the herbicidal activity of the individual compounds. In other words, the joint action of the aminopyralid+imazamox combination and the at least one herbicide B results in an enhanced activity against harmful plants in the sense of a synergy effect (synergism). For this reason, the compositions can, based on the individual components, be used at lower application rates to achieve a herbicidal effect comparable to the individual components. The compositions of the invention also show an accelerated action on harmful plants, i.e. damaging of the harmful plants is achieved more quickly in comparison with application of the individual herbicides. Moreover, the compositions of the present invention provide good pre-emergence herbicidal activity, i.e. the compositions are particularly useful for combating/controlling harmful plants before their emergence. Apart form that, the compositions of the present invention show good crop compatibility, i.e. their use in crops leads to a reduced damage of the crop plants.

As used herein, the terms "controlling" and "combating" are synonyms. As used herein, the terms "undesirable vegetation" and "harmful plants" are synonyms.

The compositions of the invention comprise the aminopyralid+imazamox combination as a first component a).

As a second component b), the compositions of the invention comprise at least one herbicide B which is selected from the at least one herbicide B from the group of the lipid biosynthesis inhibitors, acetohydroxyacid synthase inhibitors, carotenoid biosynthesis inhibitors, auxin herbicides, mitosis inhibitors, protoporphyrinogen IX oxidase inhibitors, growth substances, and a variety of other herbicides according to the groups of the HRAC classification system (see HRAC, Classification of Herbicides According to Mode of Action, http://www.plantprotection.org/hrac/MOA.html). In one embodiment a herbicide B is present, in another embodiment two herbicides B are present.

The herbicide B is selected from the groups:
b.1 lipid biosynthesis inhibitors, preferably selected from
  acetamides, such as diphenamid, napropamide, and naproanilide,
  oxyacetamides, such as anilofos, mefenacet and flufenacet,
  chloroacetanilides, such as dimethenamid, dimethenamid-P, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor and xylachlor,
  thiocarbamates, such as butylate, cycloate, di-allate, dimepiperate, EPTC, esprocarb, molinate, pebulate, prosulfocarb, thiobencarb (benthiocarb), tri-allate and vernolate, and
  benzofuranes, such as benfuresate and ethofumesate;
b.2 acetohydroxyacid synthase inhibitors, preferably selected from
  imidazolinones, such as imazapic, imazapyr, imazaquin and imazethapyr and their salts and their esters;
  sulfonylureas, such as amidosulfuron, azimsulfuron, bensulfuron, chlorimuron, chlorsulfuron, cinosulfuron, cyclosulfamuron, ethametsulfouron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrasosulfuron, rimsulfuron, sulfometuron, sulfosulfuron, thifensulfuron, triasulfuron, tribenuron, trifloxysulfuron, triflusulfuron and tritosulfuron and their salts and, in case the compounds carry a carboxyl group, their esters,
  triazolopyrimidines, such as cloransulam, diclosulam, flumetsulam, florasulam, metosulam, penoxulam and pyroxsulam and their salts and, in case of cloransulam also their esters,
  pyrimidinylthiobenzoates, such as bispyribac, pyribenzowim, pyriftalid, pyrithiobac, pyriminobac, and
  sulfonylaminocarbonyltriazolinones, such as flucarbazone, propoxycarbazone and thiencarbazone and their salts;
b.3 carotenoid biosynthesis inhibitors, preferably:
  benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon, amitrol, topramezone, tembotrione, pyrasulfotole, and picolinafen;
b.4 auxin herbicides, preferably selected from
  pyridinecarboxylic acids, such as clopyralid or picloram, or
  2,4-D or benazolin;
b.5 mitosis inhibitors, preferably selected from
  carbamates, such as asulam, carbetamid, chlorpropham, orbencarb, pronamid (propyzamid), propham, and tiocarbazil,
  dinitroanilines, such as benefin, butralin, dinitramin, ethalfluralin, fluchloralin, oryzalin, pendimethalin, prodiamine and trifluralin,
  pyridines, such as dithiopyr and thiazopyr, and
  butamifos, chlorthal-dimethyl (DCPA) or maleic hydrazide;
b.6 protoporphyrinogen IX oxidase inhibitors, preferably selected from
  diphenyl ethers, such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen and oxyfluorfen, oxadiazoles, such as oxadiargyl and oxadiazon,
cyclic imides, such as azafenidin, butafenacil, carfentrazone-ethyl, cinidon-ethyl, flumiclorac-pentyl, flumioxazin, flumipropyn, flupropacil, fluthiacet-methyl, saflufenacil, sulfentrazone and thidiazimin, and
pyrazoles, such as ET-751, JV 485 and nipyraclofen, b.7 growth substances, preferably selected from
aryloxyalkanoic acids, such as, 4-DB, clomeprop, dichlorprop, dichlorprop-P, (2,4-DP-P), fluoroxypyr, MCPA, MCPB, mecoprop, mecoprop-P, and triclopyr,
benzoic acids, such as chloramben and dicamba, and
quinolinecarboxylic acids, such as quinclorac and quinmerac.

The imidazolinones as components in herbicide A and in herbicide B may be present in the form of their racemate or in the form of the pure R- or S-enantiomers (including salts and esters as defined above). Very suitable Imidazolinones are the R-isomers, e.g. R-imazamethabenz-methyl, R-imazamox, R-imazapic, R-imazapyr, R-imazaquin, R-imazethapyr, in particular R-imazamox. These compounds are known e.g. from U.S. Pat. No. 5,973,154 and U.S. Pat. No. 6,339,158.

In one embodiment the aminopyralid/imazamox combination is combined with an oxyacetamide selected from flufenacet and mefenacet.

In a preferred embodiment the aminopyralid/imazamox combination is combined with a carotenoid biosynthesis inhibitor selected from benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon, amitrol, topramezone, tembotrione, pyrasulfotole, and picolinafen.

In another preferred embodiment the aminopyralid/imazamox combination is combined with a chloroacetanilide, preferably dimethenamid, dimethenamid-P, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor.

In another preferred embodiment the aminopyralid/imazamox combination is combined with a pyridinecarboxylic acid, preferably clopyralid or picloram.

In another preferred embodiment the aminopyralid/imazamox combination is combined with a dinitroaniline, preferably benefin, butralin, dinitramin, ethalfluralin, fluchloralin, oryzalin, pendimethalin, prodiamine or trifluralin.

In another preferred embodiment the aminopyralid/imazamox combination is combined with a diphenyl ether, preferably acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen.

In another preferred embodiment the aminopyralid/imazamox combination is combined with a quinolinecarboxylic acid, preferably quinclorac or quinmerac.

Further preferred embodiments relate to the compositions A-1 to A-330 listed in Table A, where a row of Table A corresponds in each case to a herbicidal composition comprising aminopyralid+imazamox as herbicide A and the respective herbicide B, which may include a further herbicide (herbicide B2) stated in the respective row. Preferably, the compositions described comprise the active substances in synergistically effective amounts.

TABLE A

Compositions comprising aminopyralid + imazamox (herbicide A) and one or two herbicide(s) B

| Mixture | Herbicide B | Herbicide B2 |
|---|---|---|
| A-1 | dimethenamid-P | — |
| A-2 | dimethenamid-P | amidosulfuron |
| A-3 | dimethenamid-P | Azimsulfuron |
| A-4 | dimethenamid-P | Bensulfuron-methyl |
| A-5 | dimethenamid-P | Chlorimuron-ethyl |
| A-6 | dimethenamid-P | Chlorsulfuron |
| A-7 | dimethenamid-P | Cinosulfuron |
| A-8 | dimethenamid-P | Cyclosulfamuron |
| A-9 | dimethenamid-P | Ethametsulfuron-methyl |
| A-10 | dimethenamid-P | Flazasulfuron |
| A-11 | dimethenamid-P | Flupyrsulfuron-methyl |
| A-12 | dimethenamid-P | Foramsulfuron |
| A-13 | dimethenamid-P | halosulfuron-methyl |
| A-14 | dimethenamid-P | Imazosulfuron |
| A-15 | dimethenamid-P | Iodosulfuron |
| A-16 | dimethenamid-P | Mesosulfuron |
| A-17 | dimethenamid-P | Metsulfuron-methyl |
| A-18 | dimethenamid-P | Nicosulfuron |
| A-19 | dimethenamid-P | Oxasulfuron |
| A-20 | dimethenamid-P | Primisulfuron-methyl |
| A-21 | dimethenamid-P | Prosulfuron |
| A-22 | dimethenamid-P | Pyrasosulfuron-ethyl |
| A-23 | dimethenamid-P | Rimsulfuron |
| A-24 | dimethenamid-P | Sulfometuron-methyl |
| A-25 | dimethenamid-P | Sulfosulfuron |
| A-26 | dimethenamid-P | Thifensulfuron-methyl |
| A-27 | dimethenamid-P | Triasulfuron |
| A-28 | dimethenamid-P | Tribenuron-methyl |
| A-29 | dimethenamid-P | Trifloxysulfuron |
| A-30 | dimethenamid-P | Triflusulfuron-methyl |
| A-31 | dimethenamid-P | Tritosulfuron |
| A-32 | dimethenamid-P | Cloransulam-methyl |
| A-33 | dimethenamid-P | Diclosulam |
| A-34 | dimethenamid-P | Florasulam |
| A-35 | dimethenamid-P | Flumetsulam |
| A-36 | dimethenamid-P | Metosulam |
| A-37 | dimethenamid-P | Penoxsulam |
| A-38 | dimethenamid-P | Pyroxsulam |
| A-39 | dimethenamid-P | Flucarbazone-sodium |
| A-40 | dimethenamid-P | Propoxycarbazone-sodium |
| A-41 | dimethenamid-P | Bispyribac-sodium |
| A-42 | dimethenamid-P | Pyribenzoxim |
| A-43 | dimethenamid-P | Pyriftalid |
| A-44 | dimethenamid-P | Pyrithiobac-sodium |
| A-45 | dimethenamid-P | Pyiminobac-methyl |
| A-46 | dimethenamid-P | clopyralid |
| A-47 | dimethenamid-P | picloram |
| A-48 | dimethenamid-P | 2,4-D |
| A-49 | dimethenamid-P | benazolin |
| A-50 | dimethenamid-P | clomazone |
| A-51 | dimethenamid-P | benzofenap |
| A-52 | dimethenamid-P | diflufenican |
| A-53 | dimethenamid-P | fluorochloridone |
| A-54 | dimethenamid-P | fluridone |
| A-55 | dimethenamid-P | pyrazolynate |
| A-56 | dimethenamid-P | pyrazoxyfen |
| A-57 | dimethenamid-P | isoxaflutole |
| A-58 | dimethenamid-P | isoxachlortole |
| A-59 | dimethenamid-P | mesotrione |
| A-60 | dimethenamid-P | sulcotrione |
| A-61 | dimethenamid-P | ketospiradox |
| A-62 | dimethenamid-P | flurtamone |
| A-63 | dimethenamid-P | norflurazon |
| A-64 | dimethenamid-P | amitrol |
| A-65 | dimethenamid-P | Topramezone |
| A-66 | dimethenamid-P | Tembotrione |
| A-67 | dimethenamid-P | Pyrasulfotole |
| A-68 | dimethenamid-P | picolinafen |
| A-69 | dimethenamid-P | propyzamid |
| A-70 | dimethenamid-P | carbetamid |
| A-71 | dimethenamid-P | benefin |
| A-72 | dimethenamid-P | butralin |
| A-73 | dimethenamid-P | dinitramin |
| A-74 | dimethenamid-P | ethalfluralin |
| A-75 | dimethenamid-P | fluchloralin |

TABLE A-continued

Compositions comprising aminopyralid + imazamox (herbicide A) and one or two herbicide(s) B

| Mixture | Herbicide B | Herbicide B2 |
|---|---|---|
| A-76 | dimethenamid-P | oryzalin |
| A-77 | dimethenamid-P | pendimethalin |
| A-78 | dimethenamid-P | prodiamine |
| A-79 | dimethenamid-P | trifluralin |
| A-80 | dimethenamid-P | thiazopyr |
| A-81 | dimethenamid-P | acifluorfen-sodium |
| A-82 | dimethenamid-P | bifenox |
| A-83 | dimethenamid-P | chlornitrofen |
| A-84 | dimethenamid-P | ethoxyfen |
| A-85 | dimethenamid-P | fluoroglycofen-ethyl |
| A-86 | dimethenamid-P | fomesafen |
| A-87 | dimethenamid-P | furyloxyfen |
| A-88 | dimethenamid-P | lactofen |
| A-89 | dimethenamid-P | nitrofen |
| A-90 | dimethenamid-P | nitrofluorfen |
| A-91 | dimethenamid-P | oxyfluorfen |
| A-92 | dimethenamid-P | Oxadiargyl |
| A-93 | dimethenamid-P | Oxadiazon |
| A-94 | dimethenamid-P | Azafenidin |
| A-95 | dimethenamid-P | Butafenacil |
| A-96 | dimethenamid-P | Carfentrazone-ethyl |
| A-97 | dimethenamid-P | Cinidon-ethyl |
| A-98 | dimethenamid-P | Flumiclorac-pentyl |
| A-99 | dimethenamid-P | Flumioxazin |
| A-100 | dimethenamid-P | Flumipropyn |
| A-101 | dimethenamid-P | Flupropacil |
| A-102 | dimethenamid-P | Fluthiacet-methyl |
| A-103 | dimethenamid-P | Saflufenacil |
| A-104 | dimethenamid-P | Sulfentrazone |
| A-105 | dimethenamid-P | Thidiazimin |
| A-106 | dimethenamid-P | ET-751 |
| A-107 | dimethenamid-P | JV 485 |
| A-108 | dimethenamid-P | nipyraclofen |
| A-109 | dimethenamid-P | quinclorac |
| A-110 | dimethenamid-P | quinmerac |
| A-111 | dimethenamid-P | napropamide |
| A-112 | dimethachlor | — |
| A-113 | dimethachlor | amidosulfuron |
| A-114 | dimethachlor | Azimsulfuron |
| A-115 | dimethachlor | Bensulfuron-methyl |
| A-116 | dimethachlor | Chlorimuron-ethyl |
| A-117 | dimethachlor | Chlorsulfuron |
| A-118 | dimethachlor | Cinosulfuron |
| A-119 | dimethachlor | Cyclosulfamuron |
| A-120 | dimethachlor | Ethametsulfuron-methyl |
| A-121 | dimethachlor | Flazasulfuron |
| A-122 | dimethachlor | Flupyrsulfuron-methyl |
| A-123 | dimethachlor | Foramsulfuron |
| A-124 | dimethachlor | halosulfuron-methyl |
| A-125 | dimethachlor | Imazosulfuron |
| A-126 | dimethachlor | Iodosulfuron |
| A-127 | dimethachlor | Mesosulfuron |
| A-128 | dimethachlor | Metsulfuron-methyl |
| A-129 | dimethachlor | Nicosulfuron |
| A-130 | dimethachlor | Oxasulfuron |
| A-131 | dimethachlor | Primisulfuron-methyl |
| A-132 | dimethachlor | Prosulfuron |
| A-133 | dimethachlor | Pyrasosulfuron-ethyl |
| A-134 | dimethachlor | Rimsulfuron |
| A-135 | dimethachlor | Sulfometuron-methyl |
| A-136 | dimethachlor | Sulfosulfuron |
| A-137 | dimethachlor | Thifensulfuron-methyl |
| A-138 | dimethachlor | Triasulfuron |
| A-139 | dimethachlor | Tribenuron-methyl |
| A-140 | dimethachlor | Trifloxysulfuron |
| A-141 | dimethachlor | Triflusulfuron-methyl |
| A-142 | dimethachlor | Tritosulfuron |
| A-143 | dimethachlor | Cloransulam-methyl |
| A-144 | dimethachlor | Diclosulam |
| A-145 | dimethachlor | Florasulam |
| A-146 | dimethachlor | Flumetsulam |
| A-147 | dimethachlor | Metosulam |
| A-148 | dimethachlor | Penoxsulam |
| A-149 | dimethachlor | Pyroxsulam |
| A-150 | dimethachlor | Flucarbazone-sodium |
| A-151 | dimethachlor | Propoxycarbazone-sodium |
| A-152 | dimethachlor | Bispyribac-Na |
| A-153 | dimethachlor | Pyribenzoxim |
| A-154 | dimethachlor | Pyriftalid |
| A-155 | dimethachlor | Pyrithiobac-sodium |
| A-156 | dimethachlor | Pyiminobac-methyl |
| A-157 | dimethachlor | clopyralid |
| A-158 | dimethachlor | picloram |
| A-159 | dimethachlor | 2,4-D |
| A-160 | dimethachlor | benazolin |
| A-161 | dimethachlor | clomazone |
| A-162 | dimethachlor | benzofenap |
| A-163 | dimethachlor | diflufenican |
| A-164 | dimethachlor | fluorochloridone |
| A-165 | dimethachlor | fluridone |
| A-166 | dimethachlor | pyrazolynate |
| A-167 | dimethachlor | pyrazoxyfen |
| A-168 | dimethachlor | isoxaflutole |
| A-169 | dimethachlor | isoxachlortole |
| A-170 | dimethachlor | mesotrione |
| A-171 | dimethachlor | sulcotrione |
| A-172 | dimethachlor | ketospiradox |
| A-173 | dimethachlor | flurtamone |
| A-174 | dimethachlor | norflurazon |
| A-175 | dimethachlor | amitrol |
| A-176 | dimethachlor | Topramezone |
| A-177 | dimethachlor | Tembotrione |
| A-178 | dimethachlor | Pyrasulfotole |
| A-179 | dimethachlor | picolinafen |
| A-180 | dimethachlor | propyzamid |
| A-181 | dimethachlor | carbetamid |
| A-182 | dimethachlor | benefin |
| A-183 | dimethachlor | butralin |
| A-184 | dimethachlor | dinitramin |
| A-185 | dimethachlor | ethalfluralin |
| A-186 | dimethachlor | fluchloralin |
| A-187 | dimethachlor | oryzalin |
| A-188 | dimethachlor | pendimethalin |
| A-189 | dimethachlor | prodiamine |
| A-190 | dimethachlor | trifluralin |
| A-191 | dimethachlor | thiazopyr |
| A-192 | dimethachlor | acifluorfen-sodium |
| A-193 | dimethachlor | bifenox |
| A-194 | dimethachlor | chlornitrofen |
| A-195 | dimethachlor | ethoxyfen |
| A-196 | dimethachlor | fluoroglycofen-ethyl |
| A-197 | dimethachlor | fomesafen |
| A-198 | dimethachlor | furyloxyfen |
| A-199 | dimethachlor | lactofen |
| A-200 | dimethachlor | nitrofen |
| A-201 | dimethachlor | nitrofluorfen |
| A-202 | dimethachlor | oxyfluorfen |
| A-203 | dimethachlor | Oxadiargyl |
| A-204 | dimethachlor | Oxadiazon |
| A-205 | dimethachlor | Azafenidin |
| A-206 | dimethachlor | Butafenacil |
| A-207 | dimethachlor | Carfentrazone-ethyl |
| A-208 | dimethachlor | Cinidon-ethyl |
| A-209 | dimethachlor | Flumiclorac-pentyl |
| A-210 | dimethachlor | Flumioxazin |
| A-211 | dimethachlor | Flumipropyn |
| A-212 | dimethachlor | Flupropacil |
| A-213 | dimethachlor | Fluthiacet-methyl |
| A-214 | dimethachlor | Saflufenacil |
| A-215 | dimethachlor | Sulfentrazone |
| A-216 | dimethachlor | Thidiazimin |
| A-217 | dimethachlor | ET-751 |
| A-218 | dimethachlor | JV 485 |
| A-219 | dimethachlor | nipyraclofen |
| A-220 | dimethachlor | quinclorac |
| A-221 | dimethachlor | quinmerac |
| A-222 | dimethachlor | napropamide |
| A-223 | metazachlor | — |
| A-224 | metazachlor | amidosulfuron |
| A-225 | metazachlor | Azimsulfuron |

TABLE A-continued

Compositions comprising aminopyralid + imazamox
(herbicide A) and one or two herbicide(s) B

| Mixture | Herbicide B | Herbicide B2 |
|---|---|---|
| A-226 | metazachlor | Bensulfuron-methyl |
| A-227 | metazachlor | Chlorimuron-ethyl |
| A-228 | metazachlor | Chlorsulfuron |
| A-229 | metazachlor | Cinosulfuron |
| A-230 | metazachlor | Cyclosulfamuron |
| A-231 | metazachlor | Ethametsulfuron-methyl |
| A-232 | metazachlor | Flazasulfuron |
| A-233 | metazachlor | Flupyrsulfuron-methyl |
| A-234 | metazachlor | Foramsulfuron |
| A-235 | metazachlor | halosulfuron-methyl |
| A-236 | metazachlor | Imazosulfuron |
| A-237 | metazachlor | Iodosulfuron |
| A-238 | metazachlor | Mesosulfuron |
| A-239 | metazachlor | Metsulfuron-methyl |
| A-240 | metazachlor | Nicosulfuron |
| A-241 | metazachlor | Oxasulfuron |
| A-242 | metazachlor | Primisulfuron-methyl |
| A-243 | metazachlor | Prosulfuron |
| A-244 | metazachlor | Pyrasosulfuron-ethyl |
| A-245 | metazachlor | Rimsulfuron |
| A-246 | metazachlor | Sulfometuron-methyl |
| A-247 | metazachlor | Sulfosulfuron |
| A-248 | metazachlor | Thifensulfuron-methyl |
| A-249 | metazachlor | Triasulfuron |
| A-250 | metazachlor | Tribenuron-methyl |
| A-251 | metazachlor | Trifloxysulfuron |
| A-252 | metazachlor | Triflusulfuron-methyl |
| A-253 | metazachlor | Tritosulfuron |
| A-254 | metazachlor | Cloransulam-methyl |
| A-255 | metazachlor | Diclosulam |
| A-256 | metazachlor | Florasulam |
| A-257 | metazachlor | Flumetsulam |
| A-258 | metazachlor | Metosulam |
| A-259 | metazachlor | Penoxsulam |
| A-260 | metazachlor | Pyroxsulam |
| A-261 | metazachlor | Flucarbazone-sodium |
| A-262 | metazachlor | Propoxycarbazone-sodium |
| A-263 | metazachlor | Bispyribac-sodium |
| A-264 | metazachlor | Pyribenzoxim |
| A-265 | metazachlor | Pyriftalid |
| A-266 | metazachlor | Pyrithiobac-sodium |
| A-267 | metazachlor | Pyriminobac-methyl |
| A-268 | metazachlor | clopyralid |
| A-269 | metazachlor | picloram |
| A-270 | metazachlor | 2,4-D |
| A-271 | metazachlor | benazolin |
| A-272 | metazachlor | clomazone |
| A-273 | metazachlor | benzofenap |
| A-274 | metazachlor | diflufenican |
| A-275 | metazachlor | fluorochloridone |
| A-276 | metazachlor | fluridone |
| A-277 | metazachlor | pyrazolynate |
| A-278 | metazachlor | pyrazoxyfen |
| A-279 | metazachlor | isoxaflutole |
| A-280 | metazachlor | isoxachlortole |
| A-281 | metazachlor | mesotrione |
| A-282 | metazachlor | sulcotrione |
| A-283 | metazachlor | ketospiradox |
| A-284 | metazachlor | flurtamone |
| A-285 | metazachlor | norflurazon |
| A-286 | metazachlor | amitrol |
| A-287 | metazachlor | Topramezone |
| A-288 | metazachlor | Tembotrione |
| A-289 | metazachlor | Pyrasulfotole |
| A-290 | metazachlor | picolinafen |
| A-291 | metazachlor | propyzamid |
| A-292 | metazachlor | carbetamid |
| A-293 | metazachlor | benefin |
| A-294 | metazachlor | butralin |
| A-295 | metazachlor | dinitramin |
| A-296 | metazachlor | ethalfluralin |
| A-297 | metazachlor | fluchloralin |
| A-298 | metazachlor | oryzalin |
| A-299 | metazachlor | pendimethalin |
| A-300 | metazachlor | prodiamine |
| A-301 | metazachlor | trifluralin |
| A-302 | metazachlor | thoazopyr |
| A-303 | metazachlor | acifluorfen-sodium |
| A-304 | metazachlor | bifenox |
| A-305 | metazachlor | chlornitrofen |
| A-306 | metazachlor | ethoxyfen |
| A-307 | metazachlor | fluoroglycofen-ethyl |
| A-308 | metazachlor | fomesafen |
| A-309 | metazachlor | furyloxyfen |
| A-310 | metazachlor | lactofen |
| A-311 | metazachlor | nitrofen |
| A-312 | metazachlor | nitrofluorfen |
| A-313 | metazachlor | oxyfluorfen |
| A-314 | metazachlor | Oxadiargyl |
| A-315 | metazachlor | Oxadiazon |
| A-316 | metazachlor | Azafenidin |
| A-317 | metazachlor | Butafenacil |
| A-318 | metazachlor | Carfentrazone-ethyl |
| A-319 | metazachlor | Cinidon-ethyl |
| A-320 | metazachlor | Flumiclorac-pentyl |
| A-321 | metazachlor | Flumioxazin |
| A-322 | metazachlor | Flumipropyn |
| A-323 | metazachlor | Flupropacil |
| A-324 | metazachlor | Fluthiacet-methyl |
| A-325 | metazachlor | Saflufenacil |
| A-326 | metazachlor | Sulfentrazone |
| A-327 | metazachlor | Thidiazimin |
| A-328 | metazachlor | ET-751 |
| A-329 | metazachlor | JV 485 |
| A-330 | metazachlor | nipyraclofen |
| A-331 | metazachlor | quinclorac |
| A-332 | metazachlor | quinmerac |
| A-333 | metazachlor | napropamide |

In the compositions of the present invention the relative weight ratio of aminopyralid to herbicide B is preferably in the range from 1:500 to 500:1, in particular in the range from 1:250 to 250:1 and more preferably from 100:1 to 1:100. Accordingly, in the methods and uses of the invention, aminopyralid and the at least one herbicide B are applied within these weight ratios.

The compositions of the invention may also comprise, as a component c), one or more safeners. Safeners, also termed as herbicide safeners are organic compounds which in some cases lead to better crop plant compatibility when applied jointly with specifically acting herbicides. Some safeners are themselves herbicidally active. In these cases, the safeners act as antidote or antagonist in the crop plants and thus reduce or even prevent damage to the crop plants. However, in the compositions of the present invention, safeners are generally not required. Therefore, a preferred embodiment of the invention relates to compositions which contain no safener or virtually no safener (i.e. less than 1% by weight, based on the total amount of herbicide A and herbicide B).

Suitable safeners, which can be used in the compositions according to the present invention are known in the art, e.g. from The Compendium of Pesticide Common Names (http://www.alanwood.net/pesticides/); Farm Chemicals Handbook 2000 Vol. 86, Meister Publishing Company, 2000; B. Hock, C. Fedtke, R. R. Schmidt, Herbizide, Georg Thieme Verlag, Stuttgart 1995; W. H. Ahrens, Herbicide Handbook, 7th Edition, Weed Science Society of America, 1994; and K. K. Hatzios, Herbicide Handbook, Supplement to 7th Edition, Weed Science Society of America, 1998.

Safeners include benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloracetyl)-1,3-oxazolidine, 4-(dichloroacetyl)-1-oxa-4-azaspiro[4.5]decane and oxabetrinil, as well as thereof agriculturally acceptable salts and, provided they have a carboxyl group, their agriculturally acceptable derivatives. 2,2,5-Trimethyl-3-(dichloroacetyl)-1,3-oxazolidine [CAS No. 52836-31-4] is also known under the name R-29148.4-(Dichloroacetyl)-1-oxa-4-azaspiro[4.5]decane [CAS No. 71526-07-03] is also known under the names AD-67 and MON 4660.

As safener, the compositions according to the invention particularly preferably comprise at least one of the compounds selected from the group of benoxacor, cloquintocet, cyprosulfamide, dichlormid, fenchlorazole, fenclorim, fluxofenim, furilazole, isoxadifen, mefenpyr, naphthalic anhydride, 2,2,5-trimethyl-3-(dichloroacetyl)-1,3-oxazolidine, and 4-(dichloroacetyl)-1-oxa-4-azaspiro[4.5]decane and oxabetrinil; and the agriculturally acceptable salt thereof and, in the case of compounds having a COOH group, an agriculturally acceptable derivative as defined below.

A preferred embodiment of the invention relates to compositions which contain no safener or virtually no safener (i.e. less than 1% by weight, based on the total amount of herbicide A and the at least one herbicide B) is applied.

If the compounds of herbicide compounds mentioned as herbicides B and safeners (see below) have functional groups, which can be ionized, they can also be used in the form of their agriculturally acceptable salts. In general, the salts of those cations are suitable whose cations have no adverse effect on the action of the active compounds ("agricultural acceptable").

In general, the salts of those cations are suitable whose cations have no adverse effect on the action of the active compounds ("agricultural acceptable"). Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium (hereinafter also termed as organoammonium) in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

In the compositions according to the invention, the compounds that carry a carboxyl group can also be employed in the form of agriculturally acceptable derivatives, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters. Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester. Preferred derivatives are the esters.

The compositions of the present invention are suitable for controlling a large number of harmful plants, including monocotyledonous weeds, in particular annual weeds such as gramineous weeds (grasses) including *Echinochloa* species such as barnyardgrass (*Echinochloa crusgalli* var. *crus-galli*), *Digitaria* species such as crabgrass (*Digitaria sanguinalis*), *Setaria* species such as green foxtail (*Setaria viridis*) and giant foxtail (*Setaria faberii*), *Sorghum* species such as johnsongrass (*Sorghum halepense* Pers.), *Avena* species such as wild oats (*Avena fatua*), *Cenchrus* species such as *Cenchrus echinatus*, *Bromus* species, *Lolium* species, *Phalaris* species, *Eriochloa* species, *Panicum* species, *Brachiaria* species, annual bluegrass (*Poa annus*), blackgrass (*Alopecurus myosuroides*), *Aegilops cylindrica*, *Agropyron repens*, *Apera spica-venti*, *Eleusine indica*, *Cynodon dactylon* and the like.

The compositions of the present invention are also suitable for controlling a large number of dicotyledonous weeds, in particular broad leaf weeds including *Polygonum* species such as wild buckwheat (*Polygonum convolvulus*), *Amaranthus* species such as pigweed (*Amaranthus retroflexus*), *Chenopodium* species such as common lambsquarters (*Chenopodium album* L.), *Sida* species such as prickly sida (*Sida spinosa* L.), *Ambrosia* species such as common ragweed (*Ambrosia artemisiifolia*), *Acanthospermum* species, *Anthemis* species, *Atriplex* species, *Cirsium* species, *Convolvulus* species, *Conyza* species, *Cassia* species, *Commelina* species, *Datura* species, *Euphorbia* species, *Geranium* species, *Galinsoga* species, morningglory (*Ipomoea* species), *Lamium* species, *Malva* species, *Matricaria* species, *Sysimbrium* species, *Solanum* species, *Xanthium* species, *Veronica* species, *Viola* species, common chickweed (*Stellaria media*), velvetleaf (*Abutilon theophrasti*), Hemp sesbania (*Sesbania exaltata* Cory), *Anoda cristata*, *Bidens pilosa*, *Brassica kaber*, *Capsella bursa-pastoris*, *Centaurea cyanus*, *Galeopsis tetrahit*, *Galium aparine*, *Helianthus annuus*, *Desmodium tortuosum*, *Kochia scoparia*, *Mercurialis annua*, *Myosotis arvensis*, *Papaver rhoeas*, *Raphanus raphanistrum*, *Salsola kali*, *Sinapis arvensis*, *Sonchus arvensis*, *Thlaspi arvense*, *Tagetes minuta*, *Richardia brasiliensis*, *Rumex crispus*, *Rumex obtusifolius*, *Heracleaum sphondylium*, *Aethusa cynapium*, *Daucus carota*, *Equisetum arvense* and the like.

The compositions of the present invention are also suitable for controlling a large number of annual and perennial sedge weeds including *cyperus* species such as purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), and the like.

The compositions according to the present invention are suitable for combating/controlling common harmful plants in useful plants (i.e. in crops). The compositions of the present invention are generally suitable for combating/controlling undesired vegetation in
Grain crops, including e.g.
cereals such as wheat (*Triticum aestivum*) and wheat like crops such as *durum* (*T. durum*), einkorn (*T. monococcum*), emmer (*T. dicoccon*) and spelt (*T. spelta*), rye (*Secale cereale*), triticale (*Tritiosecale*), barley (*Hordeum vulgare*);
maize (corn; *Zea mays*);
sorghum (e.g. *Sorghum bicolour*);
rice (*Oryza* spp. such as *Oryza sativa* and *Oryza glaberrima*); and
sugar cane;
Legumes (Fabaceae), including e.g. soybeans (*Glycine max.*), peanuts (*Arachis hypogaea* and pulse crops such as peas including *Pisum sativum*, pigeon pea and cowpea, beans including broad beans (*Vicia faba*), *Vigna* spp., and *Phaseolus* spp. and lentils (*lens culinanis* var.);

brassicaceae, including e.g. canola (*Brassica napus*), oilseed rape (*Brassica napus*), cabbage (*B. oeracea* var.), mustard such as *B. juncea, B. campestris, B. narinosa, B. nigra* and *B. tournefortii*; and turnip (*Brassica rapa* var.);

other broadleaf crops including e.g. sunflower, cotton, flax, linseed, sugarbeet, potato and tomato;

TNV-crops (TNV: trees, nuts and vine) including e.g. grapes, citrus, pomefruit, e.g. apple and pear, coffee, pistachio and oilpalm, stonefruit, e.g. peach, almond, walnut, olive, cherry, plum and apricot;

turf, pasture and rangeland;

onion and garlic;

bulb ornamentals such as tulips and narcissus;

conifers and deciduous trees such as *pinus*, fir, oak, maple, dogwood, hawthorne, crabapple, and *rhamnus* (buckthorn); and garden ornamentals such as petunia, marigold, roses and snapdragon.

The compositions of the present invention are in particular suitable for combating/controlling undesired vegetation in wheat, barley, rye, triticale, *durum*, rice, corn, sugarcane, *sorghum*, soybean, pulse crops such as pea, bean and lentils, peanut, sunflower, sugarbeet, potato, cotton, *brassica* crops, such as oilseed rape, canola, mustard, cabbage and turnip, turf, grapes, pomefruit, such as apple and pear, stonefruit, such as peach, almond, walnut, olive, cherry, plum and apricot, citrus, coffee, pistachio, garden ornamentals, such as roses, petunia, marigold, snap dragon, bulb ornamentals such as tulips and narcissus, conifers and deciduous trees such as *pinus*, fir, oak, maple, dogwood, hawthorne, crabapple and *rhamnus*.

The compositions of the present invention are most suitable for combating/controlling undesired vegetation in wheat, barley, rye, triticale, *durum*, rice, corn, sugarcane, *sorghum*, soybean, pulse crops such as pea, bean and lentils, peanut, sunflower, sugarbeet, potato, cotton, *brassica* crops, such as oilseed rape, canola, mustard, cabbage and turnip, turf, grapes, stonefruit, such as peach, almond, walnut, olive, cherry, plum and apricot, citrus and pistachio.

If not stated otherwise, the compositions of the invention are suitable for application in any variety of the aforementioned crop plants.

The compositions according to the invention can also be used in crop plants which are resistant to one or more herbicides owing to genetic engineering or breeding, which are resistant to one or more pathogens such as plant pathogenous fungi to genetic engineering or breeding, or which are resistant to attack by insects owing to genetic engineering or breeding. Suitable are for example crop plants, preferably corn, wheat, sunflower, rice, canola, oilseed rape, soybeans or lentils which are resistant to herbicidal AHAS inhibitors, such as, for example, imazamethabenz, imazamox, imazapic, imazapyr, imazaquin, imazethapyr, or sulfonylureas or crop plants which, owing to introduction of the gene for Bt toxin by genetic modification, are resistant to attack by certain insects.

The compositions of the present invention can be applied in conventional manner by using techniques as skilled person is familiar with. Suitable techniques include spraying, atomizing, dusting, spreading or watering. The type of application depends on the intended purpose in a well known manner; in any case, they should ensure the finest possible distribution of the active ingredients according to the invention.

The compositions can be applied pre- or post-emergence, i.e. before, during and/or emergence of the undesirable plants. When the compositions are used in crops, they can be applied after seeding and before or after the emergence of the crop plants. The compositions invention can, however, also be applied prior to seeding of the crop plants.

It is a particular benefit of the compositions according to the invention that they have a very good pre-emergence herbicide activity, i.e. they show a good herbicidal activity against not yet emerged undesirable plants. Thus, in a preferred embodiment of invention, the compositions are applied pre-emergence, i.e. during and/or after, the emergence of the undesirable plants. It is particularly advantageous to apply the mixtures according to the invention post emergent when the undesirable plant starts with leaf development up to flowering. Since the composition show good crop tolerance, even when the crop has already emerged, they can be applied after seeding of the crop plants and in particular during or after the emergence of the crop plants.

In any case the components of herbicide A and the at least one herbicide B can be applied simultaneously or in succession.

The compositions are applied to the plants mainly by spraying, in particular foliar spraying. Application can be carried out by customary spraying techniques using, for example, water as carrier and spray liquor rates of from about 10 to 2000 l/ha or 50 to 1000 l/ha (for example from 100 to 500 l/ha). Application of the herbicidal compositions by the low-volume and the ultra-low-volume method is possible, as is their application in the form of microgranules.

If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

In the case of a post-emergence treatment of the plants, the herbicidal mixtures or compositions according to the invention are preferably applied by foliar application. Application may be effected, for example, by usual spraying techniques with water as the carrier, using amounts of spray mixture of approx. 20 to 1000 l/ha.

The required application rate of the composition of the pure active compounds, i.e. of aminopyralid, herbicide B and optionally safener or herbicide D depends on the density of the undesired vegetation, on the development stage of the plants, on the climatic conditions of the location where the composition is used and on the application method. In general, the application rate of the composition (total amount of pyroxasulfone, herbicide B and optional further actives) is from 15 to 5000 g/ha, preferably from 20 to 2500 g/ha of active substance.

The required application rates of aminopyralid are generally in the range from 0.1 g/ha to 500 g/ha and preferably in the range from 1 g/ha to 200 g/ha or from 5 g/ha to 100 g/ha of active substance.

The required application rates of imazamox are generally in the range from 0.1 g/ha to 200 g/ha and preferably in the range from 1 g/ha to 100 g/ha or from 5 g/ha to 75 g/ha of active substance. Following that the herbicide A is the aminopyralid/imazamox combination in a ratio range of 1000:1 to 1:1000, preferably 100:1 to 1:100, more preferred 10:1 to 1:10.

The required application rates of the herbicide B (total amount of herbicide B) are generally in the range from 0.1 g/ha to 5000 g/ha and preferably in the range from 1 g/ha to 3000 g/ha or from 2 g/ha to 1500 g/ha of active substance.

The required application rates of the safener, if applied, are generally in the range from 1 g/ha to 5000 g/ha and preferably in the range from 2 g/ha to 5000 g/ha or from 5 g/ha to 5000 g/ha of active substance. Preferably no safener or virtually no safener is applied and thus the application rates are below 5 g/ha, in particular below 2 g/ha or below 1 g/ha.

The compositions of this embodiment are particularly suitable for controlling mono- and dicotyledonous weeds and sedge weeds, in particular *Aegilops Cylindrica, Agropyron repens, Alopecurus myosuroides, Avena fatua, Brassica* spec., *Brachiaria* spec., *Bromus* spec., *Echinochloa* spec., *Lolium* spec., *Phalaris* spec., red rice, *Setaria* spec., *Sorghum* spec., *Abuthilon theoprasti, Amarantus* spec., *Brassica kaber, Capsella bursa-pastoris, Chenopodium* spec., *Cyperus* spec., *Euphorbia* spec., *Geranium* spec., *Ipomoea* spec., *Polygonum* spec., *Raphanus raphanistrum, Sinapis arevensis, Sysimbrium* spec. and *Thlaspi arvense.*

The compositions of this embodiment are in particular suitable for combating undesired vegetation in wheat, barley, rye, triticale, *durum*, rice, corn, sugarcane, *sorghum*, soybean, pulse crops such as pea, bean and lentils, peanut, sunflower, sugarbeet, potato, cotton, *brassica* crops, such as oilseed rape, canola, mustard, cabbage and turnip, turf, grapes, stonefruit, such as peach, almond, walnut, olive, cherry, plum and apricot, citrus, pistachio, conifers and deciduous treas.

If not stated otherwise, the compositions of this embodiment are suitable for application in any variety of the aforementioned crop plants.

The compositions of this embodiments are most suitable for application in soybean, peanut, puls crops such as pea, bean and lentils, sugarcane, oil palm, conifers and deciduous trees.

The compositions of this embodiment can preferably be used in crops which tolerate and/or are resistant to the action of AHAS herbicides, preferably in crops which tolerate and/or are resistant to the action of imidazolinone herbicides. The resistance and or tolerance to said herbicides may be achieved by conventional breeding and/or by genetic engineering methods. Crops which are tolerant to AHAS herbicides (e.g. tolerant to imidazolinone herbicides) are known for example from EP-A 154 204 (MGI Pharma Inc.). Such crops are for example marketed by BASF under the trade name CLEARFIELD. Examples for such crops are maize, canola, oilseed rape, sunflower, rice, soybean, lentils and wheat.

The present invention also relates to formulations of the compositions according to the present invention. The formulations contain, besides the composition, at least one organic or inorganic carrier material. The formulations may also contain, if desired, one or more surfactants and, if desired, one or more further auxiliaries customary for crop protection compositions.

The formulation may be in the form of a single package formulation containing both the herbicide A and the at least one herbicide B together with liquid and/or solid carrier materials, and, if desired, one or more surfactants and, if desired, one or more further auxiliaries customary for crop protection compositions. The formulation may be in the form of a two package formulation, wherein one package contains a formulation of the herbicide A while the other package contains a formulation of the at least one herbicide B and wherein both formulations contain at least one carrier material, if desired, one or more surfactants and, if desired, one or more further auxiliaries customary for crop protection compositions. In the case of two package formulations the formulation containing the herbicide A and the formulation containing the herbicide B are mixed prior to application. In case the herbicide A itself is a two package formulation the composition is in the form of a three-pack formulation. Preferably the mixing is performed as a tank mix, i.e. the formulations are mixed immediately prior or upon dilution with water.

In the formulation of the present invention the active ingredients, i.e. aminopyralid, imazamox, herbicide B and optional further actives are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules. Depending on the formulation type, they comprise one or more liquid or solid carriers, if appropriate surfactants (such as dispersants, protective colloids, emulsifiers, wetting agents and tackifiers), and if appropriate further auxiliaries which are customary for formulating crop protection products. The person skilled in the art is sufficiently familiar with the recipes for such formulations. Further auxiliaries include e.g. organic and inorganic thickeners, bactericides, antifreeze agents, antifoams, colorants and, for seed formulations, adhesives.

Suitable carriers include liquid and solid carriers. Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof. Solid carriers include e.g. mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers™-types, Borregaard), phenolsulfonic acids, naphthalenesulfonic acids (Morwet types, Akzo Nobel) and dibutylnaphthalenesulfonic acid (Nekal® types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol® types Clariant), polycarboxylates (BASF SE, Sokalan® types), polyalkoxylates, polyvinylamine (BASF SE, Lupamine® types), polyethyleneimine (BASF SE, Lupasol® types), polyvinylpyrrolidone and copolymers thereof.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R. T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide® MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

To prepare emulsions, pastes or oil dispersions, the active the components, as such or dissolved in an oil or solvent, can be homogenized in water by means of wetting agent, tackifier, dispersant or emulsifier. Alternatively, it is possible to prepare concentrates consisting of active substance, wetting agent, tackifier, dispersant or emulsifier and, if desired, solvent or oil, and these concentrates are suitable for dilution with water.

Powders, materials for spreading and dusts can be prepared by mixing or concomitant grinding of the active the components a) and b) and optionally safener c) with a solid carrier.

Granules, e.g. coated granules, impregnated granules and homogeneous granules, can be prepared by binding the active ingredients to solid carriers.

The formulations of the invention comprise a herbicidally effective amount of the composition of the present invention. The concentrations of the active the active ingredients in the formulations can be varied within wide ranges. In general, the formulations comprise from 1 to 98% by weight, preferably 10 to 60% by weight, of active ingredients (sum of pyroxasulfone, herbicide B and optionally further actives). The active ingredients are employed in a purity of from 90% to 100%, preferably 95% to 100% (according to NMR spectrum).

The active compounds A and B as well as the compositions according to the invention can, for example, be formulated as follows:

1. Products for Dilution with Water

A Water-Soluble Concentrates 10 parts by weight of active compound (or composition) are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound (or composition) are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound (or composition) are dissolved in 75 parts by weight of an organic solvent (eg. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound (or composition) are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound (or composition) are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound (or composition) are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound (or composition) are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound (or composition), 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound (or composition) are ground finely and mixed intimately with 95 parts by weight of finely divided kaolin. This gives a dusting powder with an active compound content of 5% by weight.

J Granules (GR, FG, GG, MG)

0.5 parts by weight of active compound (or composition) are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound (or composition) are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

It may furthermore be beneficial to apply the compositions of the invention alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

USE EXAMPLES

The effect of the herbicidal compositions according to the invention of herbicides A and B and, if appropriate, safener on the growth of undesirable plants compared to the herbicidally active compounds alone was demonstrated by the following greenhouse experiments:

The test plants have been seeded, separately for each species, in plastic containers in sandy loamy soil containing 5% of organic matter.

For the post emergence treatment, the plants were first grown to the 2 leaf station (GS 12). Here, the herbicidal compositions were suspended or emulsified in water as distribution medium and sprayed using finely distributing nozzels.

The plants have been cultivated due to there individual requirements at 10-25° C. and 20-35° C. The plants were irrigated due to there necessity.

The respective herbicides A and/or safener were formulated as 10% by weight strength suspension concentrate and introduced to the spray liquor with the amount of solvent system used for applying the active compound. Herbicide B and/or safener were used as commercially available formulations and introduced to the spray liquor with the amount of solvent system used for applying the active compound. In the examples, the solvent used was water.

Aminiopyralid was used as commercial aquaeous solution having an active ingredient concentration of 240 g/l (Milestone™).

Imazamox was used as a commercial aqueous solution having an active ingredient concentration of 120 g/l (Raptor®).

Metazachlor was used as a commercial suspension concentrate having an active ingredient concentration of 500 g/l (Butisan S®).

Clopyralid was used as commercial aqueous solution having an active ingredient concentration of 100 g/l (Lontrel®).

In the following experiments, the herbicidal activity for the individual herbicide compounds (solo and mixture applications), the herbicidal succession was assessed 14 days after treatment (DAT).

The evaluation for the damage on undesired weeds caused by the chemical compositions was carried out using a scale from 0 to 100%, compared to the untreated control plants. Here, 0 means no damage and 100 means complete destruction of the plants.

The plants used in the greenhouse experiments belonged to the following species:

| Code | Scientific Name |
|---|---|
| CAPBP | Capsella bursa-pasturis |
| CENCY | Centauria cyanus |
| LAMPU | Lamium purpureum |
| MATIN | Matricaria inodora |
| MATCH | Matricaria chamomilla |
| MERAN | Mercurialis annua |
| PAPRH | Papaver rhoeas |
| SSYOF | Sysimbrium officinale |
| STEME | Stellaria media |
| THLAR | Thlaspi arvense |
| VERPE | Veronica persica |
| VIOAR | Viola arvensis |

The value E, which is to be expected if the activity of the individual compounds is just additive, was calculated using the method of S. R. Colby (1967) "Calculating synergistic and antagonistic responses of herbicide combinations", weeds 15, p. 22ff.

Colby calculation for ternary mixtures:

$$E = (X + Y + Z) - \frac{(X*Y + X*Z + Y*Z)}{100} + \frac{(X*Y*Z)}{10000}$$

where:

X = effect in percent using herbicide A at an application rate a;

Y = effect in percent using herbicide B at an application rate b;

Z = effect in percent using herbicide C at an application rate c;

E = expected effect (in %) of A+B+C at application rates a+b+c

Tables 1 to 2 relate to the herbicidal activity, in greenhouse trials, of the individual actives and the combination in post-emergence application 14 DAT.

TABLE 1

Application in post-emergence aminopyralid + imazamox + metazachlor

| | solo application | | | | | | combination A + B + C | | COLBY |
|---|---|---|---|---|---|---|---|---|---|
| | aminopyralid (A) | | imazamox (B) | | metazachlor (C) | | | | |
| weed | use rate g ai/ha | % activity 28 DAT | use rate g ai/ha | % activity 28 DAT | use rate g ai/ha | % activity 28 DAT | use rate g ai/ha | % activity 28 DAT | expected % activity 28 DAT |
| CAPBP | 5 | 10 | 20 | 90 | 187 | 0 | 5 + 20 + 187 | 95 | 91 |
| CAPBP | 2.5 | 0 | 20 | 90 | 187 | 0 | 2.5 + 20 + 187 | 95 | 90 |
| MATIN | 5 | 60 | 20 | 65 | 187 | 60 | 5 + 20 + 187 | 95 | 94 |
| MATIN | 2.5 | 35 | 20 | 65 | 187 | 60 | 2.5 + 20 + 187 | 95 | 91 |
| PAPRH | 5 | 15 | 20 | 35 | 187 | 30 | 5 + 20 + 187 | 75 | 61 |
| PAPRH | 2.5 | 0 | 20 | 35 | 187 | 30 | 2.5 + 20 + 187 | 65 | 54 |
| MERAN | 2.5 | 70 | 20 | 90 | 187 | 15 | 2.5 + 20 + 187 | 98 | 97 |

TABLE 1-continued

Application in post-emergence aminopyralid + imazamox + metazachlor

| | solo application | | | | | | combination A + B + C | | COLBY |
|---|---|---|---|---|---|---|---|---|---|
| | aminopyralid (A) | | imazamox (B) | | metazachlor (C) | | | | |
| weed | use rate g ai/ha | % activity 28 DAT | use rate g ai/ha | % activity 28 DAT | use rate g ai/ha | % activity 28 DAT | use rate g ai/ha | % activity 28 DAT | expected % activity 28 DAT |
| MATCH | 5 | 75 | 20 | 70 | 187 | 10 | 5 + 20 + 187 | 100 | 93 |
| MATCH | 2.5 | 40 | 20 | 70 | 187 | 10 | 2.5 + 20 + 187 | 95 | 84 |
| THLAR | 2.5 | 30 | 20 | 90 | 187 | 0 | 2.5 + 20 + 187 | 95 | 93 |
| VIOAR | 5 | 10 | 20 | 0 | 187 | 15 | 5 + 20 + 187 | 70 | 24 |
| VIOAR | 2.5 | 10 | 20 | 0 | 187 | 15 | 2.5 + 20 + 187 | 65 | 24 |

TABLE 2

Application in post-emergence aminopyralid + imazamox + clopyralid

| | solo application | | | | | | combination A + B + C | | COLBY |
|---|---|---|---|---|---|---|---|---|---|
| | aminopyralid (A) | | imazamox (B) | | clopyralid (C) | | | | |
| weed | use rate g ai/ha | % activity 28 DAT | use rate g ai/ha | % activity 28 DAT | use rate g ai/ha | % activity 28 DAT | use rate g ai/ha | % activity 28 DAT | expected % activity 28 DAT |
| CAPBP | 10 | 25 | 20 | 90 | 30 | 0 | 10 + 20 + 30 | 95 | 93 |
| CAPBP | 5 | 10 | 20 | 90 | 30 | 0 | 5 + 20 + 30 | 95 | 91 |
| CAPBP | 2.5 | 0 | 20 | 90 | 30 | 0 | 2.5 + 20 + 30 | 95 | 90 |
| CAPBP | 10 | 25 | 10 | 80 | 120 | 10 | 10 + 10 + 120 | 90 | 87 |

The invention claimed is:

1. A ternary herbicidal composition comprising:
   a) a herbicide A which is 4-amino-3,6-dichloropyridine-2-carboxylic acid and 2-[(RS)-4-isopropyl-4-methyl-5-oxo-2-imidazolin-2-yl]-5-methoxymethylnicotinic acid;
   and
   b) at least one herbicide B selected from the group consisting of chloroacetanilides, pyridinecarboxylic acids, and quinolinecarboxylic acids, wherein the relative amount of herbicide A to the at least one herbicide B is in synergistically effective amounts.

2. The composition according to claim 1, wherein the herbicide B is selected from the group consisting of the chloroacetanilides.

3. The composition according to claim 1, wherein the herbicide B is selected from the group consisting of the pyridinecarboxylic acids.

4. The composition according to claim 1, additionally containing a safener.

5. The composition according to claim 1, containing no safener.

6. The composition as claimed claim 1, wherein the relative amount of herbicide A to the at least one herbicide B is in synergistically effective amounts.

7. The composition as claimed in claim 1, wherein the relative amount of herbicide A to the at least one herbicide B is from about 1:1 to 1:500.

8. An herbicide formulation comprising the composition as claimed in claim 1 and at least one solid or liquid carrier.

9. The composition according to claim 1, wherein the herbicide B is selected from the group consisting of dimetenamid, dimethenamid-P, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor and xylachlor.

10. The composition according to claim 1, wherein the herbicide B is selected from the group consisting of clopyralid and picloram.

11. The composition according to claim 1, wherein the herbicide B is selected from the group consisting of quinclorac and quinmerac.

12. A method for controlling undesirable vegetation, which comprises applying a composition as claimed in claim 1 to plants to be controlled or their habitat, wherein the plants are crops of wheat, barley, rye, triticale, *durum*, rice, corn, sugarcane, *sorghum*, soybean, pulse crops, peanut, sunflower, sugarbeet, potato, cotton, *brassica* crops, turf, grapes, pomefruit, stonefruit, citrus, coffee, pistachio, garden ornamentals, bulb ornamentals, conifers or deciduous trees.

13. The method as claimed in claim 12, wherein the herbicides A and B are applied simultaneously or in succession.

14. The method of claim 13, wherein the herbicide B is selected from the group consisting of the chloroacetanilides.

15. The method of claim 13, wherein the herbicide B is selected from the group consisting of the pyridinecarboxylic acids.

16. The method of claim 12, wherein the composition additionally comprises a safener.

17. The method of claim 12, wherein the composition contains no safener.

18. The method of claim 12, wherein the relative amount of herbicide A to the at least one herbicide B is from about 1:1 to 1:500.

19. The method of claim 12, wherein the herbicide B is selected from the group consisting of the chloroacetanilides.

20. The method of claim 12, wherein the herbicide B is selected from the group consisting of the pyridinecarboxylic acids.

* * * * *